United States Patent [19]

Bicher

[11] Patent Number: 5,624,908
[45] Date of Patent: Apr. 29, 1997

[54] ANTINEOPLASTIC COMPOSITIONS

[75] Inventor: Haim I. Bicher, Tarzana, Calif.

[73] Assignee: Valley Cancer Institute, Los Angeles, Calif.

[21] Appl. No.: 487,293

[22] Filed: Jun. 7, 1995

Related U.S. Application Data

[62] Division of Ser. No. 76,013, Jun. 11, 1993, Pat. No. 5,449,663.

[51] Int. Cl.$^6$ .......................... A61K 31/70; C07H 03/02; A61N 01/30
[52] U.S. Cl. ................... 514/23; 536/4.1; 604/20; 607/1
[58] Field of Search .................. 514/23; 536/4.1; 604/20; 607/1

[56] References Cited

U.S. PATENT DOCUMENTS 5,449,663  9/1995  Bicher ........................................... 514/23

*Primary Examiner*—John Kight
*Assistant Examiner*—Howard C. Lee

[57] ABSTRACT

Anti-cancer compositions containing chiral monosaccharides and methods of their use are disclosed herein. The compositions, exhibiting cytostatic and cytotoxic properties with regard to neoplastic cells are formulated using the L-isomeric form of monosaccharides. A preferred embodiment of the invention employs the L-isomeric form of glucose with a pharmaceutically acceptable carrier. The compositions may be used alone or as an adjunct to other forms of cancer therapy. They are useful in combination with all major forms of cancer therapy including surgery, biological and chemical therapies, radiation therapy, and hyperthermia. In addition to increasing the mortality rate of neoplastic cells, these compositions can reduce the metastatic potential of the tumor, and slow the growth of the malignancy.

13 Claims, 11 Drawing Sheets

ANTINEOPLASTIC COMPOSITIONS

BACKGROUND OF THE INVENTION

This is a division of U.S. patent application Ser. No. 08/076,013, filed Jun. 11, 1993, now U.S. Pat. No. 5,449,663.

FIELD OF THE INVENTION

The present invention relates to the use of selected chiral carbohydrates in cancer therapy and processes for their application. More particularly, the invention relates to the use of L-isomers of monosaccharides having cytotoxic and cytostatic properties. The selected compounds may be used alone or as an adjunct to other forms of cancer therapy. They are useful in conjunction with major forms of cancer therapy including surgery, biological and chemical therapies, radiation therapy, and hyperthermia. The administration of therapeutically effective amounts of L-monosaccharides increases the susceptibility of neoplastic cells to toxic elements. In addition to increasing mortality rate of neoplastic cells, these agents reduce the metastatic potential of the tumor, and slow the growth of the malignancy.

DESCRIPTION OF RELATED ART

It has been estimated that well over one million new cases of cancer will be diagnosed in 1993 and over 5,000,000 people will succumb to the disease. The causes of cancer are complex and involve an elaborate interplay between environmental factors and the genetic material of the cell. Environmental factors involved in the development of cancers may be chemical, physical or biological in nature. Among the environmental factors are three major physical carcinogens, namely ionizing radiation, ultraviolet radiation and the presence of foreign bodies such as asbestos. Chemical carcinogens, both natural and man-made, tend to be compounds which complex directly with DNA and introduce errors in the DNA base sequence during replication. Biological factors include viruses, parasites, and hormones which have been implicated in mammalian carcinogenesis.

Cancer is a disease that develops when the orderly relationship between cell division and cell differentiation becomes disoriented. In normal mammalian systems the proliferation of cells is restricted to non-differentiated stem cells which ordinarily reproduce to replace mature, differentiated cells. As the proliferating stem cell differentiates, it loses the capacity to divide and reproduce. Conversely, in a cancerous system, dividing cells generally lose the capacity to differentiate and, with it, any natural constraints on their ability to reproduce.

Cancers arising in tissues having ectodermal or endodermal origins are generally called carcinomas while those derived from glands are called adenocarcinomas. Cancers arising in tissues derived from the mesoderm are called sarcomas while those of lymphhematopoietic origin are lymphomas and leukemia. Though they occur in many different types of tissue and exhibit different characteristics the primary features shared by most malignancies are anaplasia, invasion, and metastasis.

Initially cancer develops in a single cell which has been transformed through some external factor. In some cells, a single mutational event can lead to neoplastic transformation, but for most tumors it is evident that carcinogenesis is a multi-step process. The vast majority of human cancers appear to involve the accumulation of genetic damage and eventual transformation of the affected tissue. Following the transformation of the cell, tumor initiation begins with development of a clonal cluster of independently proliferating cells. In this phase no tissue destruction is evident, but cancer cells are present at their site of origin. Neoplastic cells may associate to form solid tumors or be widely disseminated in physiological systems such as bone marrow or lymphatic neoplasms. In the case of solid tumors the tissue can acquire the ability to metastasize and invade distal areas of the body through the bloodstream or lymphatic system.

The specific histology of the tumor and progression of the cancer often determine what form of treatment or combination of treatments will be used to treat the disease. Major approaches to the treatment of cancer involve surgery, radiation therapy, chemotherapy, hypothermia and immunotherapy using biological agents. These modalities often complement each other and are commonly used together, producing synergistic effects. Surgery, radiation and hyperthermia are the most effective in treating localized malignancies and together result in a cure in about 40% of all newly diagnosed cases. However non-localized neoplasms and metastatic tumors dictate the use of chemical or biological based therapies which operate throughout the body. Systemic administration of a combination of chemotherapeutic agents may cure another 10% to 15% of all patients. However, while advances in cancer treatment have been achieved using integrated therapeutic strategies, efficacious limitations still exist and patient results are often less than satisfactory.

Radiation therapy has proven effective in controlling a variety of tumors and is used in over half of all cancer cases. In addition to being used in conjunction with surgery, it often comprises the primary treatment for a number of tumor types including breast cancer, head and neck cancer, cervical cancer, brain tumors, lung cancers and certain stages of lymphoma. In general there are two major methods for delivery in radiation: teletherapy wherein external beam of radiation is aimed at the tumor site and brachytherapy, where the radiation sources are placed within or near the target. Different levels or particular forms of radiation, each of which has advantages for specific clinical situations, can be used to facilitate local control of tumor growth. As such, radiation therapy may be tailored to reflect the type of tumor or the individual needs of the patient.

Despite these advantages, the use of radiotherapy is still constrained by limitations inherent in the process. Normal tissues vary a great deal in the amount of radiation they can safely tolerate, and this tolerance limits the total acceptable dose of radiation. Moreover, radiation will kill only those cancer cells that receive sufficient linear energy transfer in the presence of molecular oxygen. The ionization of oxygen is believed to produce free radicals which are toxic to the neoplastic cells. Yet, many tumors occur in regions of tissue containing cells which are poorly oxygenated and prove to be relatively radiation resistant. It has been reported that these hypoxic cells may be less radiosensitive by a factor of up to three. As a result, hypoxic cell sensitizers are being tested in an effort to improve the therapeutic effects of tolerable doses of radiation. Nevertheless radioresistance still remains a primary impediment to effective preferential killing of cancer cells.

As with radiation, hyperthermia has been shown to be tumoricidal in vitro and in vivo and has given encouraging results in clinical trials. Selective destruction of neoplastic cells appears to be a result of their sensitivity due to their active cellular metabolism. Among other effects, hyperthermia can cause irreversible damage to cancer cell respiration and interfere with synthesis of nucleic acids and proteins. In addition hyperthermia often disrupts the membrane of the malignant cells leading to their apparent autolytic destruction. It is thought that the subsequent modification of the tumor bed environment also contributes to the destruction of cancerous growths.

In addition to the direct cytotoxic effects of hyperthermia, heat is known to sensitize tissue to ionizing radiation. While hypoxic cells are as sensitive to hyperthermia as oxygenated cells, hyperthermia may inhibit the ability of hypoxic or partially hypoxic cells to recover from sublethal radiation injury. Many studies employing hyperthermia at 41° C. to 43° C. with low dose radiation have achieved remarkable regressions when compared with hyperthermia alone. Further, hyperthermia has often been found to increase the efficacy of anti-cancer drugs by altering the cellular environment and resulting metabolism. In addition it has been reported that hyperthermia may stimulate an immunological response by increasing the exposure of tumor antigens.

Selective stimulation of a patient's immune system to combat neoplasms has become an increasingly potent weapon as the discovery of tumor specific antigens has increased in recent years. Immunotherapy, consisting of both humoral and cell-mediated responses may be stimulated generally or directed at select antigens unique to cancer cells. Once a tumor cell expresses a recognizable antigen, antibodies, phagocytes, natural killer cells, cytotoxic T lymphocytes and lymphokine-activated killer cells may all be employed to eliminate the exposed malignancy. While immunotherapy has been very successful in treating non-localized neoplasms such as leukemia, it has not proved as efficacious against solid tumors. Therefore immunotherapy is often used in combination with other treatments or for suppression of metastasis following the elimination of a localized tumor.

Whichever form of treatment or combination thereof is selected, it is predicated on exploiting the differences between healthy cells and neoplastic cells. Transformed cells exhibit a number of biochemical and regulatory anomalies in comparison with healthy cells, providing an approach for non-surgical cancer treatments. For instance transformed cells often express anomalous glycoproteins on the cell surface, leading to insufficient environmental modulation of their activities. These modified proteins may preclude normal contact inhibition and tissue recognition thus allowing the cancer to spread. Yet at the same time they may also constitute a unique surface antigen. Such antigens serve as a marker and greatly facilitate the detection and eradication of a malignancy. Another important therapeutic distinction is the relatively rapid division of cancerous cells and corresponding increase in the rate of cellular metabolism. With the exception of immunotherapy, most cancer treatments tend to exploit some aspect of this accelerated reproduction to selectively terminate neoplastic cells.

To support this elevated reproductive rate cellular metabolic processes undergo a corresponding increase in tempo. It is well documented that transport systems used in the uptake of such needed nutrients as sugars, amino acids and nucleosides frequently function at higher capacity in transformed cells. Transport of glucose, its non-metabolizable analogues deoxyglucose and 3-0-methyl glucose, mannose, galactose, and glycocyamine all increase with transformation. In addition, transport of certain amino acids, such as glutamine, arginine and glutamic acid are escalated. Even analogues that are not incorporated into proteins such as cycloleucine and alpha-amino isobutyric acid also experienced increased uptake after transformation of cultured cells. This massive influx of nutrients appears to continue regardless of the efficiency of cellular reactions or the actual rate of production of essential cellular components.

For instance, cancer cells are known to consume large amounts of glucose as a source of energy permitting the exaggerated use of amino acids and nucleosides in the synthesis of DNA. Further it has been shown that many cancers are almost entirely dependant on glucose for their energy requirements. Exploiting this trait by supplying excess glucose, the aerobic glycolysis of tumor cells can be stimulated in vivo to a very high extent. However, due to substrate deficiencies, it appears that many cancer cells take in much more glucose than they can metabolize efficiently and, as a consequence, excrete large amounts of lactic acid. This leads to a lower pH value in the malignant cells which can increase the susceptibility of the tumor to various therapies.

Accordingly, it is an object of the invention to provide a means for producing cytotoxic and cytostatic effects in neoplastic tissue without injuring healthy cells.

It is a further object of the present invention to enhance the cytotoxic and cytostatic effects of cancer therapies.

It is another object of the present inventions to provide compositions useful for the reduction or elimination of malignant tissue in a mammalian system.

SUMMARY OF THE INVENTION

Generally stated the present invention accomplishes the above-described objectives by providing formulations and compositions containing enantiomeric forms of commonly occurring carbohydrates. More particularly it has been surprisingly discovered that the administration of the L-isomer of selected monosaccharides has cytotoxic and cytostatic effects on neoplastic tissue. Further, the administration of these compounds in therapeutically effective dosages appears to cause little or no damage to non-malignant cells. Thus, the L-isomers of selected monosaccharides, and in particular L-glucose, may be employed as clinically useful anti-cancer agents for various localized and non-localized malignancies. The selected compounds may be used alone or as an adjunct to other forms of cancer therapy. It was unexpectedly found that the administration of therapeutically effective quantities of isomeric monosaccharides increases the susceptibility of neoplastic cells to toxic factors. Therefore, following the administration of these L-isomers, the cells of various types of localized and non-localized tumors are selectively sensitized to adjunct therapies. The isomeric compounds are useful in conjunction with major forms of cancer therapy including surgery, biological and chemical therapies, radiation therapy, and hyperthermia. Further the L-isomers are effective against selected cancers including some types of carcinomas, adenocarcinomas, sarcomas, lymphomas and leukemias. In addition to increasing the mortality rate of neoplastic cells, these agents reduce the metastatic potential of the tumor, and slow the growth of the malignancy.

Another important facet of the present invention is the lack of toxic side effects which affords the ability to reduce or eliminate the discomfort inherent in conventional cancer therapies. Treatments involving radiation or chemotherapeutic procedures are generally accompanied by a great deal of unavoidable pain and discomfort due to damage to healthy cells. In contrast, the use of L-isomeric forms of monosaccharides have proved to be non-toxic to healthy tissue and not to cause any discomfort when administered in therapeutically effective dosages. Even if the monosaccharides of the present invention are administered in concert with conventional therapies, their use allows a dosage reduction of damaging radiation or chemotherapeutic agents. The compositions and processes disclosed herein therefore are able to eliminate or at least reduce the patient discomfort during cancer therapy.

In general the therapeutic cancer treatment of the present invention consists of:

administering a therapeutically effective quantity of at least one L-isomer of a monosaccharide to a mammalian host containing one or more transformed cells.

More specifically the active component of the instant invention may be any L-isomer of a hexose or pentose. Depending on its use the isomeric compound may be formulated with just a carrier or with other chemical or biological agents. Further, the L-isomer may be administered in either a straight chain form or cyclic form without affecting the efficacy of the treatment. The delivery technique used in the treatment is not critical and may consist of any one of a number of methods including oral administration and intravenous and intramuscular injection. It may also be injected directly into the tumor bed itself.

Further objects, features, and advantages of the present invention will become apparent to those skilled in the art from a consideration of the following detailed description when considered in combination with the following drawings

DETAILED DESCRIPTION OF EXEMPLARY EMBODIMENTS

Figure 1:
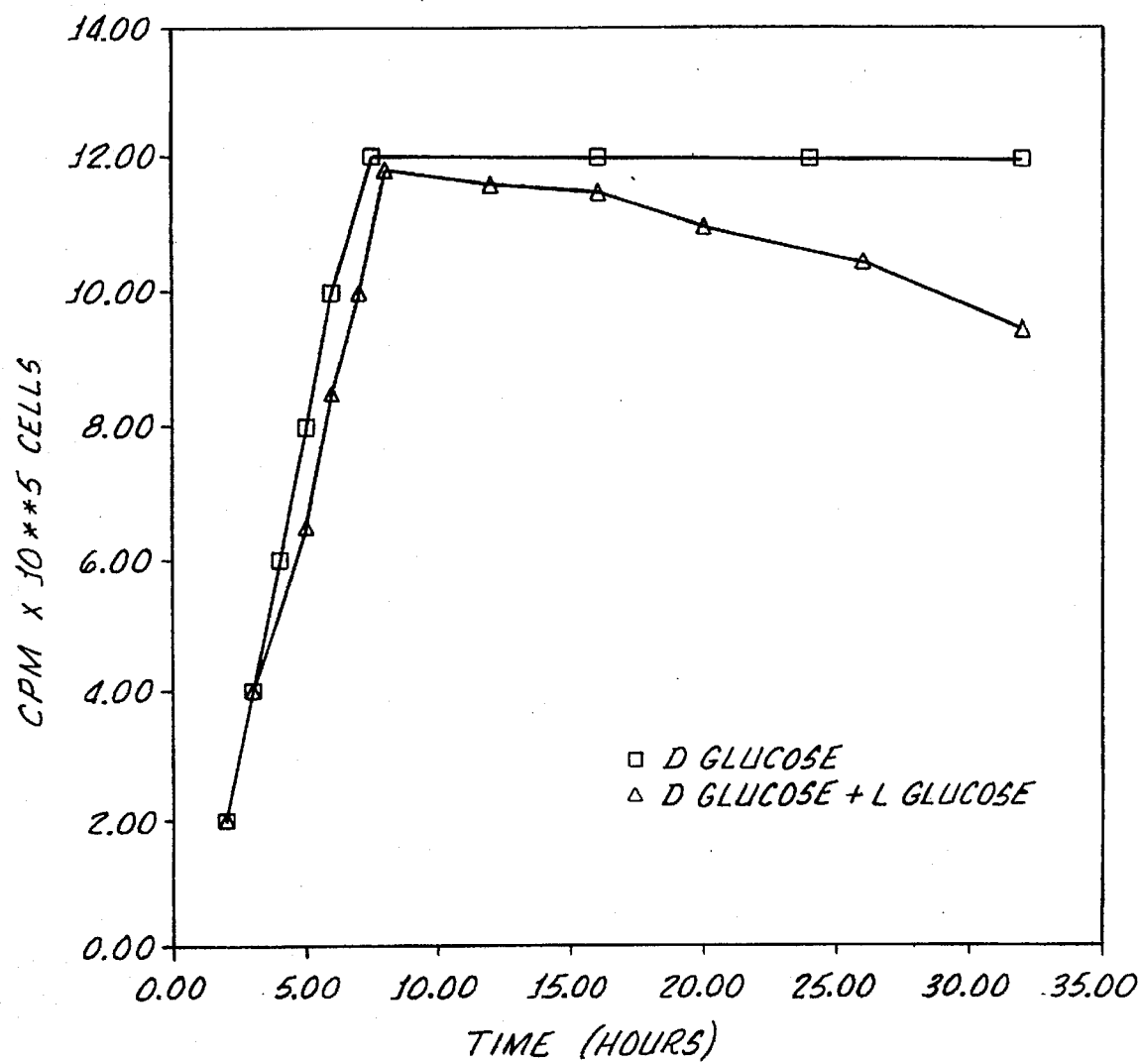
FIG. 1 is a graphical representation of the effects of L-glucose on the growth of non-cancerous CHO cells. The cells were grown in media with and without L-glucose.

Spatial arrangement of the groups around the asymmetric carbon of a certain stereoisomeric form of glyceraldehyde is arbitrarily called the D configuration while the opposite arrangement is called the L configuration. This connotation of the D and L refers to spatial configuration only and is not an indication of the direction of rotation of the plane of polarized light by the sugar. The referenced carbon atom regarding D or L configuration is, for sugars containing more than one asymmetric carbon atom, the asymmetric carbon atom farthest removed from the active site of the sugar. That is, the carbon farthest removed from the aldehyde or ketone end of the molecule and adjacent to the terminal group.

Glucose or any other monosaccharide can be isolated in two crystalline forms represented as (+) and (−) which have different physical properties. Among the differences is the ability to rotate polarized light. Samples that rotate polarized light to the right are called dextrorotatory or (+) while those that rotate polarized light to the left are known as levorotatory or (−). This empirically derived optical rotation is not correlated with the absolute configuration in any simple way. Therefore the L-isomer of a sugar can be either dextrorotatory or levorotatory depending on the crystal rotation of polarized light.

In hexoses and pentoses the ring structure or intramolecular hemiacetal form is so much more stable than the non-cyclic form that it is almost exclusively found in nature. Due to the tetrahedral angles between the carbon bonds, the carbonyl group preferably reacts with the fourth or fifth carbon of the sugar to form a hemiacetal. Hemiacetals with five-membered rings are known as furanoses while hemiacetals with six membered rings are known as pyranoses. Both forms appear to be active and for the purposes of this disclosure any discussion of a monosaccharide therapy is applicable to both the cyclic and non-cyclic L-isomers.

The L-isomeric forms of carbohydrates are found in nature but are rarely biologically active. Where they do occur, it has been reported that the isomeric interaction with the organism invariably differs. For example, a particular chiral molecule may be essential for the proper functioning of an organism whereas its mirror image is not used at all. While it is known that L-isomers of fucose and rhamnose are used in specific metabolic processes, the involvement of most L-carbohydrate isomers in cellular operations remains unclear.

While general mechanisms of isomeric carbohydrate interactions with biological systems remain indeterminate, the anti-cancer effects of the present invention are clear. In addition to exhibiting unexpected cytotoxic and cytostatic properties, the L-monosaccharides disclosed herein have shown a remarkable ability to enhance the efficacy of several conventional cancer therapies. By employing the L-isomeric forms of carbohydrates as tumor sensitizing agents, it was unexpectedly discovered that tumoricidal activities of other cancer therapies were greatly amplified. The use of these selected stereoisomeric forms of sugars can greatly increase the efficiency of radiation, hyperthermic, chemotherapeutic and biologically mediated techniques of tumor eradication. Further, the selected stereoisomers can also be used in conjunction with surgery to reduce the possibility of metastasis or a malignant recurrence.

Major forms of treatment compatible with the compositions disclosed herein are radiation, hyperthermia and surgery. The L-isomer compositions may be used to dramatically increase the effectiveness of both local and whole body hyperthermia. Similarly the invention can be used to potentiate the use of radiation in treating localized and non-localized tumors. Radiation has traditionally been ineffective in treating localized, hypoxic tumors without the use of external sources of oxygen. Tumors sensitized with the present compositions tend to respond better to various doses of radiation. This would allow the reduction of radiation employed and thus eliminate many of the unpleasant side effects. Finally, the compositions of the present invention may be used alone or in combination with other treatments to reduce the risk of recurrence after surgery.

In accordance with the teachings of the present invention, the L-isomeric form of the sugar can be formulated to include a variety of different pharmaceutically acceptable carriers. These carriers, which may include salts, gelling agents, buffers, or other matrix materials are designed to preserve the efficacious properties of the monosaccharides and facilitate the administration of the compound to a number of different tissues. Delivery methods may include oral or parenteral routes and may be conducted over any period. Specific examples are injections at the tumor site or injections delivered intramuscularly, intravenously, intra-arterially or subcutaneously. Other methods may include implanting a release system or topical applications. Further, the carrier may be formulated to include other pharmaceutically active compounds which may or may not be potentiated by the chiral monosaccharide.

The following nonlimiting examples are offered as being illustrative of the properties of exemplary compositions of the present invention.

EXAMPLE I

L-Glucose Does Not Affect Normal Cell Viability

Human Embryo Intestinal Cells (Noncancerous Cells)

An experiment was run to determine if varying concentrations of L-glucose had any effect on normal healthy human cells.

Healthy intestinal cells of a human embryo were obtained and grown using techniques well known in the art. More specifically cell cultures were initiated by seeding $1 \times 10^6$ cells in 5 ml of 199 media in 25 ml flasks. This medium was supplemented with 10% fetal calf serum, 80 µg/ml gentamicin and contained approximately 1 mg/ml D-glucose. The cells were seeded and incubated under humid atmospheric conditions with the addition of 5% $CO_2$. After 48 hours L-glucose is dissolved in complete media and added to the flasks to supply final concentrations of 1, 3 and 6 mg/ml. Corresponding amounts of D-glucose were added to separate flasks as a control. After 48 hours under these conditions the media was changed back to fresh starting media without L-glucose or extra D-glucose. Colonies were counted on the 14th day of incubation and yielded the following survival rates based on a media control:

D-glucose 6 mg/ml (98%) L-glucose 6 mg/ml (97%)

D-glucose 3 mg/ml (115%) L-glucose 3 mg/ml (101%)

D-glucose 1 mg/ml (119%) L-glucose 1 mg/ml (101%)

The results show that healthy human cells grow normally in the presence of L-glucose.

EXAMPLE II

L-Glucose Does Affect Neoplastic Cell Viability

Human colorectal adenocarcinoma (HT-29)

Studies were conducted to determine if L-glucose has cytotoxic effects on cancerous cells.

Human colorectal adenocarcinoma cell line HT-29 was obtained and cultured using techniques well known in the art. Cells were grown in the RPMI-1640 media (Sigma) with 10% fetal calf serum and gentamicin (80 mg/ml). This media contains approximately 2 mg/ml of D-glucose. Cells in the exponential phase of growth were taken from the bottom of the flask, counted, and diluted with complete media. 4.5 ml of media was then seeded with approximately $1 \times 10^6$ cells in three 25 ml flasks and incubated in oxic atmospheric conditions with 5% $CO_2$.

After 48 hours L-glucose and D-glucose were dissolved in complete medium at different concentrations and added to the flasks in a volume of 0.5 ml, giving final concentrations of added glucose equal to 1, 3 and 6 mg/ml (5.5, 16.5, 33.3 mM). The day when the glucose was added is designated as day 0.

After 14 days of incubation flasks with cells were stained and counted. In control flasks containing media only the colonies were found to have an 18.9% plating efficiency. This mean number of colonies were taken as 100%. The survival rates are as follows:

D-Glucose 6 mg/ml (110%) L-glucose 6 mg/ml (74.9%)

L-glucose 3 mg/ml (101%)

L-glucose 1 mg/ml (111%)

While there may be some statistical variation in the results, the decline in cell viability at 6 mg/ml L-glucose is striking. Comparable reductions in cell growth and cell survival were also obtained using other malignant cell lines such as human ovarian adenocarcinoma (CaOv) and FAF 28 Chinese Hamster Fibroblasts.

EXAMPLE III

Normal Cells and Cancer Cells Exhibit Different Growth Rates in the Presence of L-Glucose Rat Mammary Tumor Cells (9L-glioma)

Gliomas are radio resistant tumors which exhibit highly efficient mechanisms for cellular and DNA repair under both oxic and hypoxic conditions. As such, conventional cancer therapies such as radiation and hyperthermia have only been used with limited success against these tumors. This particular glioma cell tumor line was isolated from a rat mammary tumor and was provided by U.C. San Francisco Brain Tumor Center. To show the dramatic effects of L-glucose on neoplastic cells, a non-cancerous Chinese Hamster Ovary cell line was also subjected to L-glucose during growth.

Both cell lines were maintained using standard cell culturing techniques. Cultures for the experiment were begun by seeding cells in 5 ml of media using 25 ml flasks. Approximately $10^5$ CHO cells were used and $5 \times 10^5$ 9L glioma cells were used to inoculate the appropriate flasks. Select flasks had L-glucose added to the media prior to seeding. The cells were grown under humid, oxic atmospheric conditions at 37° C. with 5% $CO_2$. Growth was monitored using an inverted microscope with data points initially being taken every two hours.

Figure 2:
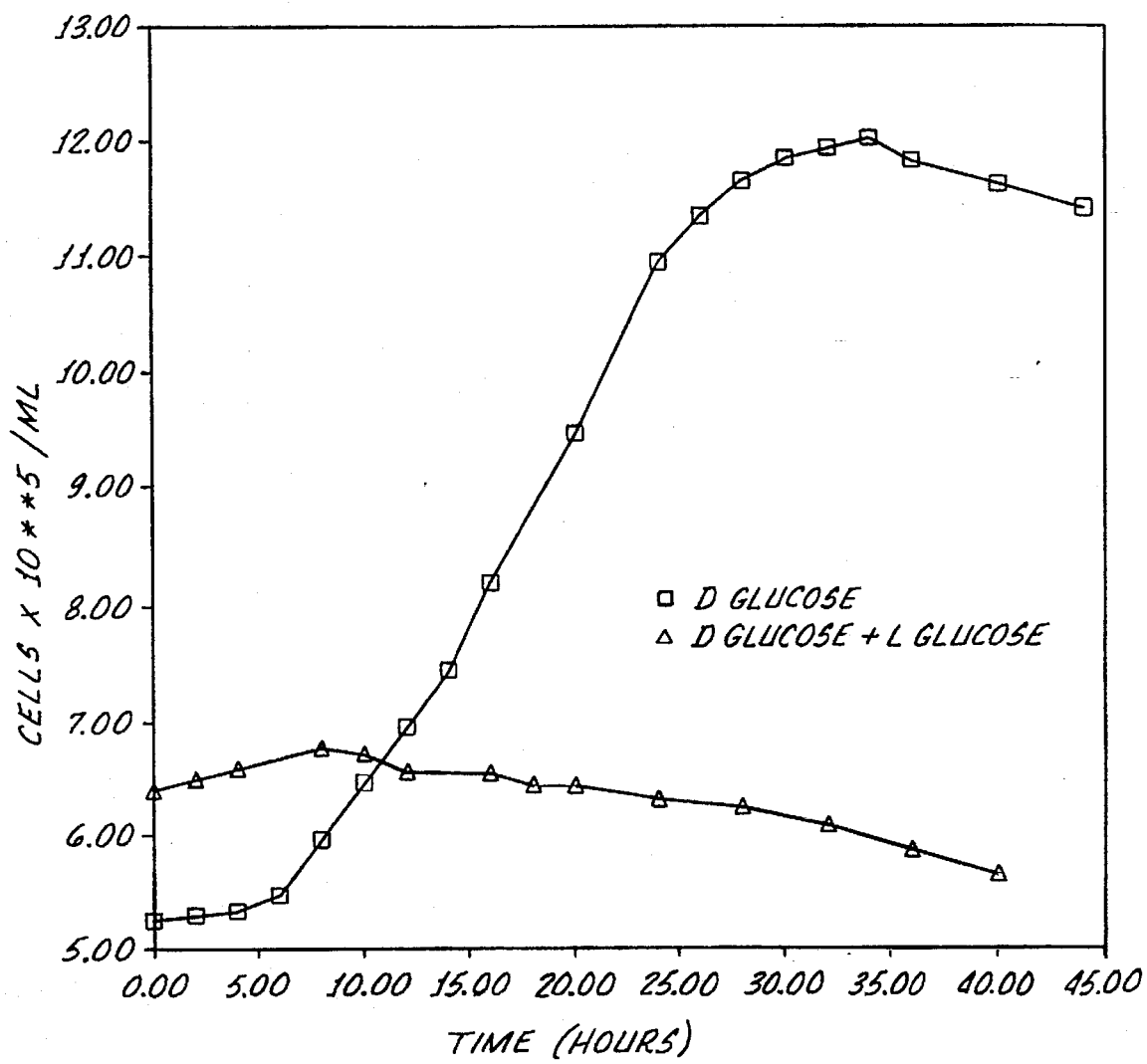
FIG. 2 is a is a graphical representation of the effects of L-glucose on the growth of 9L Glioma tumor cells. The cells were grown in media with and without L-glucose.

The results of the experiment are presented in FIGS. 1 and 2, with the growth curves of the non-cancerous CHO cells shown in FIG. 1 and the growth curves of 9L glioma tumor cells shown in FIG. 2. While there is some statistical scattering present in the curves of FIG. 1, they are essentially the same. As with Example I, these results clearly indicate that L-glucose has little or no adverse effects on non-tumor cells at these concentrations.

Conversely, as shown in FIG. 2, there is a dramatic effect on the growth of the 9L glioma tumor cells when subjected to the same concentration of L-glucose. This cytostatic effect is clearly manifested even though D-glucose was present in the media. The curves indicate that the tumor cells grown in the presence of L-glucose never entered an exponential growth phase and concentrations never increased much above initial inoculation values. The L-glucose prevented them from using the wealth of nutrients present in the fresh media. In contrast, the tumor cells grown without L-glucose in the media rapidly entered an exponential growth phase and doubled the number of cells.

From these results it is apparent that L-glucose exerts a cytostatic effect on malignant cells while not compromising the growth of normal mammalian cells.

EXAMPLE IV

L-Glucose Exhibits Cytostatic Effects on Tumor Cells

Rat Mammary Tumor Cells (9L-glioma)

In order to further demonstrate the cytostatic effects of L-glucose on neoplastic cells studies were performed using various concentrations of the monosaccharide. 9L glioma tumor cells were grown under oxic conditions in the presence of various amounts of both L-glucose and D-glucose. The tumor cell line was the same as the one used in Example III.

9L glioma cell cultures for the experiment were begun by seeding cells in 5 ml of media using 25 ml flasks. Initial concentration of cells in culture was adjusted to below $2\times10^5$ cells/ml for each experiment. The pH of the media was adjusted to approximately 7.2 to 7.4. Flasks had various amounts of L-glucose and D-glucose added to the media prior to seeding with the tumor cells. The cells were incubated under humid atmospheric conditions at 37° C. with 5% $CO_2$. Growth was monitored for a period of three to four days.

Figure 3:
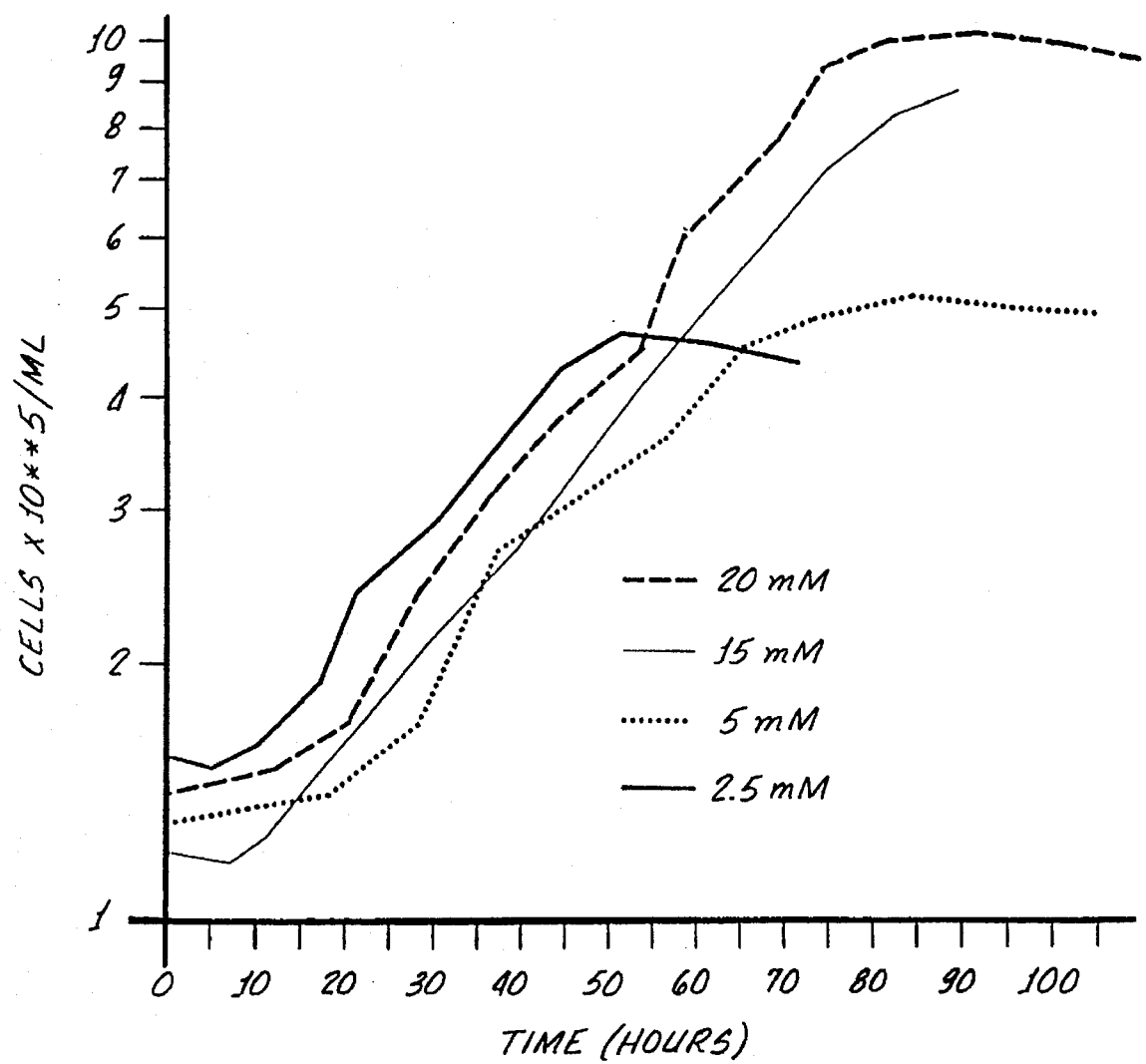
FIG. 3 is a graphical representation of the growth of 9L Glioma cells in four different concentrations of D-glucose.

To gauge the effect of L-glucose on the tumor cells a baseline was established using four different concentrations of D-glucose. As shown in FIG. 3, 9L glioma cells were grown in the presence of 2.5, 5, 15 and 20 mM D-glucose. The cultures were started at a concentration approximately $1.4\times10^5$ cell/ml and in each case exhibit a short lag growth phase of less than eight hours. As may be seen, the ultimate concentration of viable cells is proportional to the amount of D-glucose in the media. While the concentration of cells at 2.5 mM is only half of the values obtained at 15 mM or 20 mM, the actual growth rate does not appear to be dependent upon the concentration of D-glucose.

Figure 4:
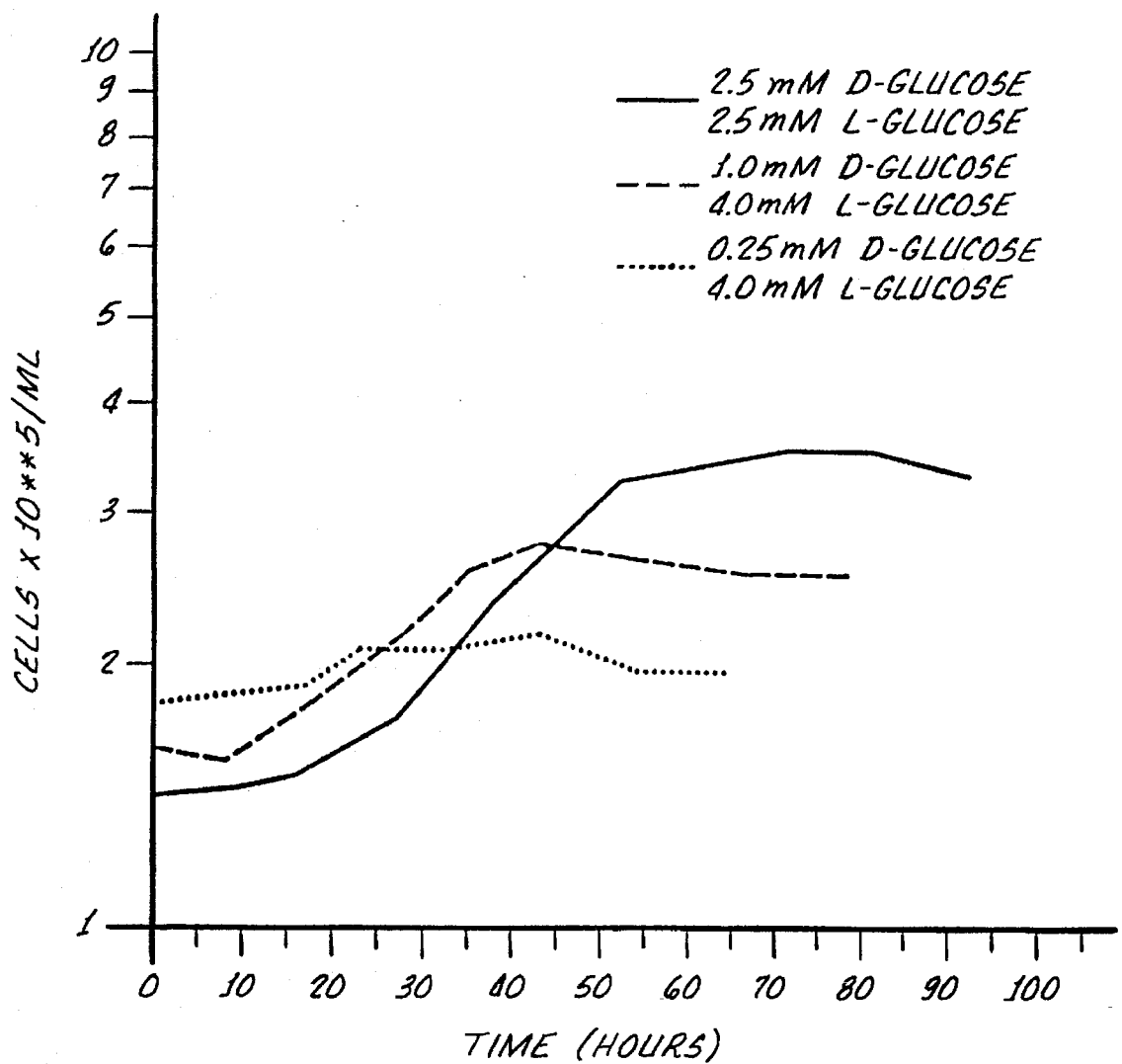
FIG. 4 indicates the effects of D-glucose and L-glucose in varying concentrations on the growth of 9L Glioma cells. The total concentration of both types of glucose is between 4 mM and 5 mM.

FIG. 4 shows the growth of 9L glioma cells in the presence of various concentrations of L-glucose. Although the ratio of L-glucose to D-glucose was varied, the racemic glucose concentration was maintained between 4 and 5 mM. The tumor cells were grown in L to D ratios of 1:1, 4:1 and 16:1 with corresponding concentrations of L-glucose at 2.5 mM, 4 mM and 4 mM respectively.

The growth at all three ratios appears slower than the growth of the tumor cells in 5 mM of D-glucose as shown in FIG. 3. Essentially there was no growth at the highest L-glucose concentration. Further, the final concentration of cells grown in the presence of L-glucose is less than the value obtained with just D-glucose. As expected the concentration of cells decrease as the amount of L-glucose is increased. These results indicate that the L/D glucose ratio is an important factor affecting cell division and consequently cell doubling time.

Figure 5:
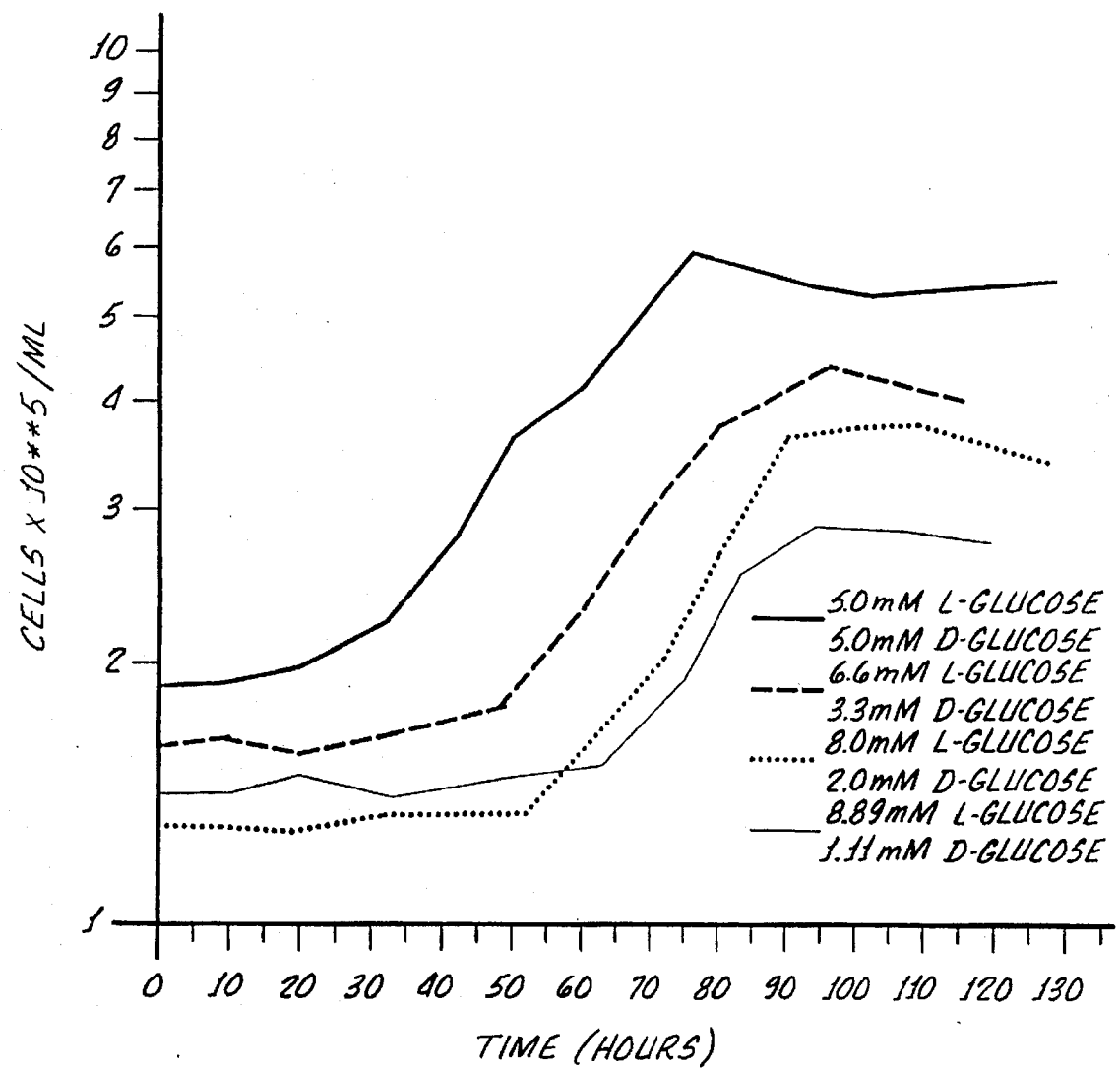
FIG. 5 represents the effects of media containing varying amounts of D-glucose and L-glucose on the growth of 9L Glioma cells. The total concentration of both types of glucose is 10 mM.

The experiment represented in FIG. 5 corresponds to the experiment of FIG. 4 except that the racemic concentration of glucose was held steady at 10 mM. The L/D glucose ratios were 1:1, 2:1, 4:1, and 8:1 corresponding to absolute L-glucose concentrations of 5 mM, 6.6 mM, 8 mM and 8.9 mM respectively.

As with FIG. 4 a relatively low growth rate with an extended lag phase is exhibited by the cells. At all ratios except 1:1 the lag phase is drawn out to approximately 50 hours or approximately 20% longer than cells grown without L-glucose. This extended lag time corresponds to a relatively longer doubling time and slower tumor growth.

Figure 6:
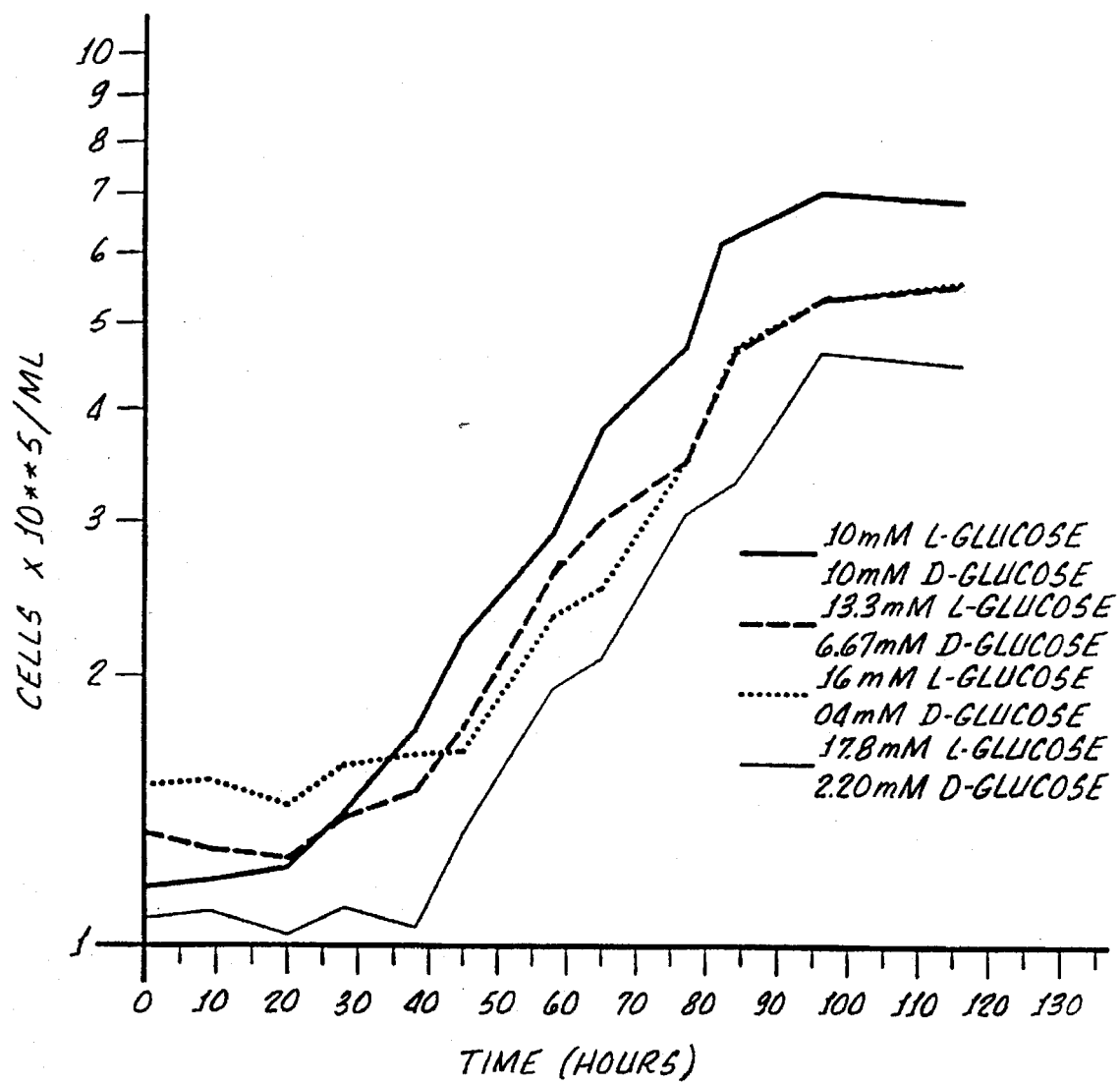
FIG. 6 represents the effects of media containing varying amounts of D-glucose and L-glucose on the growth of 9L Glioma cells. The total concentration of both types of glucose in 20 mM.

As shown in FIG. 6, a similar experiment was run using a racemic glucose concentration of 20 mM. Again the L/D glucose ratios were 1:1, 2:1, 4:1 and 8:1 corresponding to absolute L-glucose concentrations of 10 mM, 13.3 mM, 16 mM and 17.8 mM respectively. Once again the same growth pattern is observed though the prolonged lag time is less pronounced. Such a result is to be expected as the absolute concentration of D-glucose is increased. In addition, the absolute concentration of cells for all L/D ratios except 1:1 is well below the 20 mM D-glucose control plotted in FIG. 3.

The doubling times of 9L glioma cells were also determined. Results of those calculations are presented in Table I and show that cell growth is notably sluggish in the presence of L-glucose.

TABLE 1

Doubling Time of 9L Tumor Line Culture Population in the Presence of L-Glucose and D-Glucose

| Medium Composition | Doubling Time [h] |
| --- | --- |
| D-glucose only | |
| 2.5 mM | 23 |
| 5 mM | 25.5 |
| 15 mM | 24.5 |
| 20 mM | 24 |
| L-glucose + D-glucose (10 mM) | |
| 5 mM + 5 mM | 31 |
| 6.6 mM + 3.3 mM | 30 |
| 8 mM + 2 mM | 29 |
| 8.89 mM + 1.11 mM | 32 |
| L-glucose + D-glucose (20 mM) | |
| 10 mM + 10 mM | 26 |
| 13.3 mM + 6.67 mM | 26 |
| 16.0 mM + 4 mM | 29.5 |
| 17.8 mM + 2.2 mM | 30 |

These results conclusively show that the presence of L-glucose interferes with the growth of malignant cells. The extended lag time dictated by various concentrations of L-glucose corresponds to slower tumor growth. Further, the consistently lower concentration of cells in the presence of L-glucose indicates that there is an attendant cytotoxic effect.

EXAMPLE V

L-Glucose Enhances Cytolstatic and Cytotoxic Effects of Hyperthermic Therapy

Human Ovarian Cancer (CaOv)

The potentiation of hyperthermic therapy by L-glucose was demonstrated using a human ovarian cancer (CaOv) cell line. Cells were cultured and grown under normal atmospheric and hypoxic conditions. These cells were then subjected to hyperthermia for a short period in the presence of L-glucose and D-glucose and, after further incubation, were counted to determine survival rates and growth rates.

Human ovarian cancer cells (CaOv) were obtained and cultured using techniques well known in the art. Cultures were begun by seeding cells in 5 ml of 199 media supplemented with 10% fetal calf serum and 80 µg/ml gentamicin. The cells were then incubated for 24 hours at 37° C. under humid atmospheric conditions with 5% $CO_2$.

Following this incubation period, hypoxic conditions were generated in a number of the flasks by flushing them with a low oxygen gas mixture. The flasks were gassed with a mixture of 2% oxygen, 5% $CO_2$ and 93% nitrogen for a period of twenty seconds and immediately replugged with rubber stoppers. The remaining flasks were maintained at atmospheric oxygen concentrations of about 21%. Following this treatment, both sets of flasks were incubated at 37° C. for an additional 24 hours.

At this point 6 mg/ml L-glucose or 6 mg/ml D-glucose was added to select flasks while maintaining atmospheric conditions. Flasks of oxic and hypoxic cells having L-glucose or D-glucose were then incubated at 41° C. for 2 hours. Control flasks with no added glucose were also treated with heat for 2 hours. In addition, other flasks containing L-glucose or D-glucose were not subjected to elevated temperatures. Finally non-heated cultures of oxic and hypoxic cells without added glucose were used to derive a baseline.

Following the hyperthermic treatment of selected flasks, all the cells were incubated for 72 hours at 37° C. while maintaining the respective atmospheric conditions. After 72 hours the mean number of cells per colony was determined using an inverted microscope. Subsequently the media in all flasks was changed to more nutritious RPMI-1640 supplemented with 10% fetal bovine serum. Survival rate and growth rate for each set of cells was determined and is shown in FIGS. 7–10.

Figure 7:
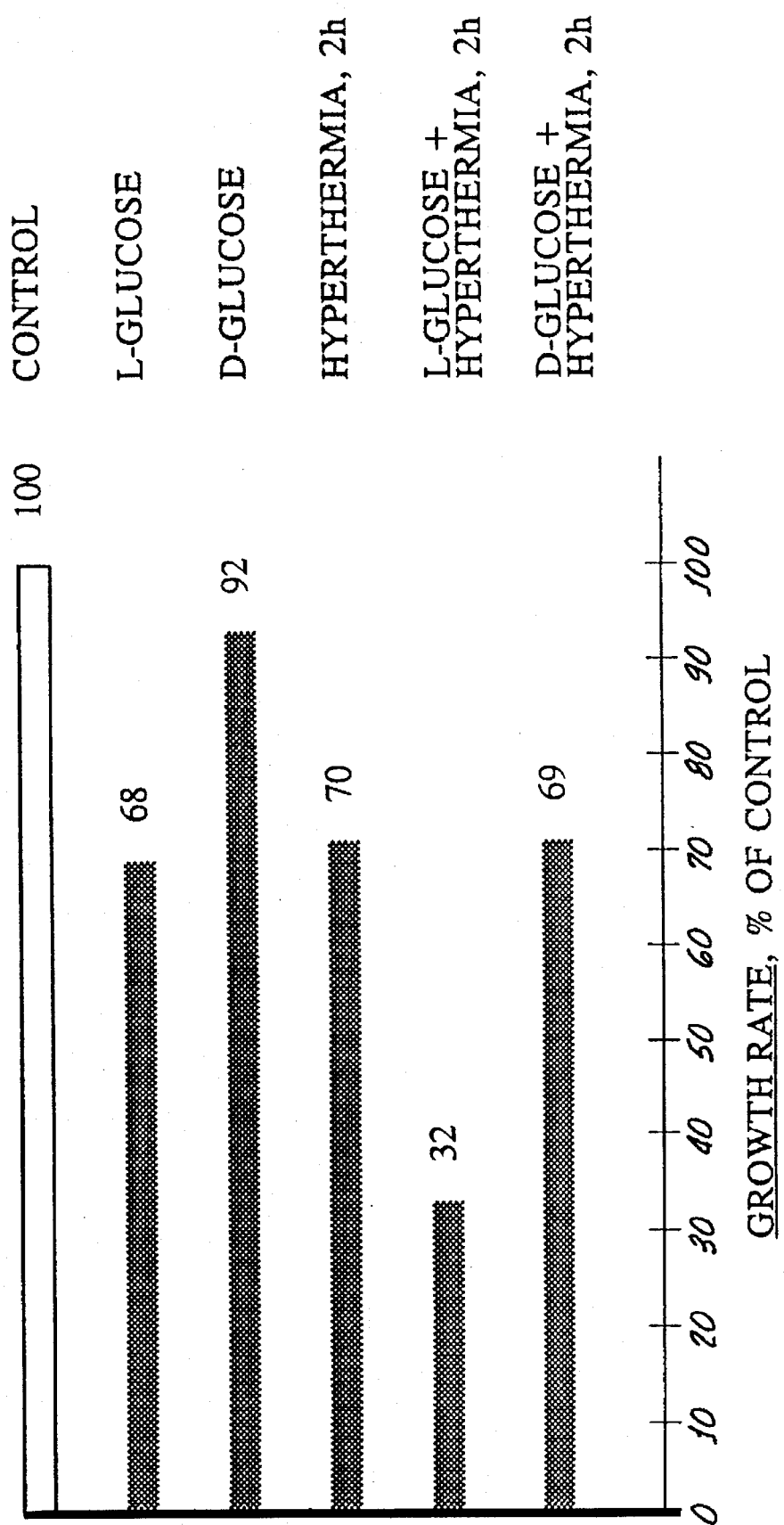
FIG. 7 represents the cytostatic effects exhibited by both stereoisomers of glucose during hyperthermic treatments of CaOv cells. The heat therapy was conducted at 41° C. under oxic conditions for two hours.
Figure 8:
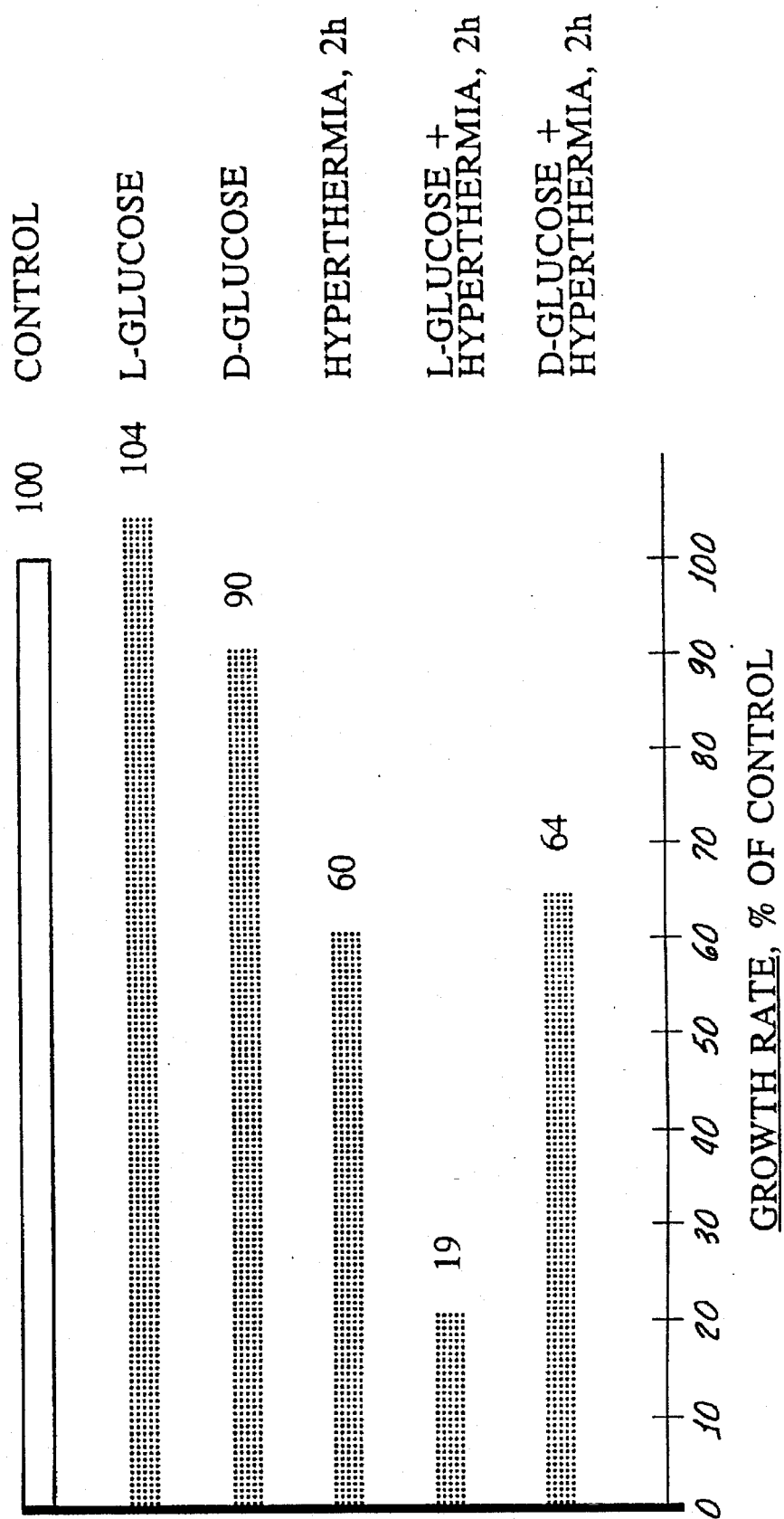
FIG. 8 represents the cytostatic effects exhibited by both stereoisomers of glucose during hyperthermic treatments of CaOv cells. The heat therapy was conducted at 41° C. under hypoxic conditions for two hours.

More specifically, FIG. 7 shows the effects of hyperthermia on the growth rate of CaOv cells in the presence of L-glucose or D-glucose and an oxic environment. Similarly, FIG. 8 shows the effects of hyperthermia on cells under hypoxic conditions with both L-glucose and D-glucose. When L-glucose was combined with hyperthermia the cells showed a dramatic decrease in growth rate whether grown under oxic or hypoxic conditions. Growth rates slow to 20% of the control under hypoxic conditions and approximately 33% when the procedure is carried out in the presence of oxygen. In sharp contrast, hyperthermia without the use of L-glucose does not reduce the growth rate of the CaOv cells below 60% of the control values.

Figure 9:
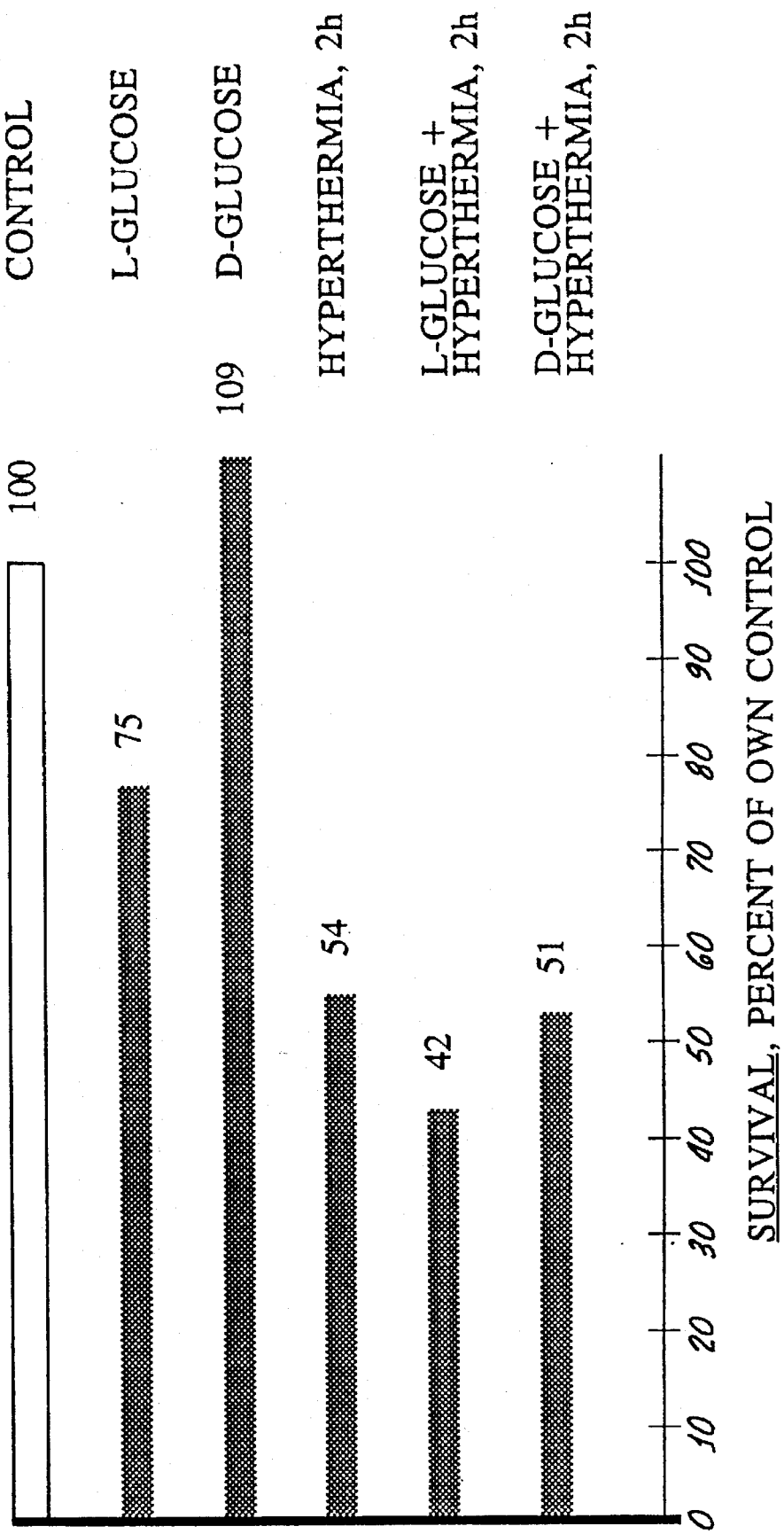
FIG. 9 represents the cytotoxic effects exhibited by both stereoisomers of glucose during hyperthermic treatments of CaOv cells. The heat therapy was conducted at 41° C. under oxic conditions for two hours.
Figure 10:
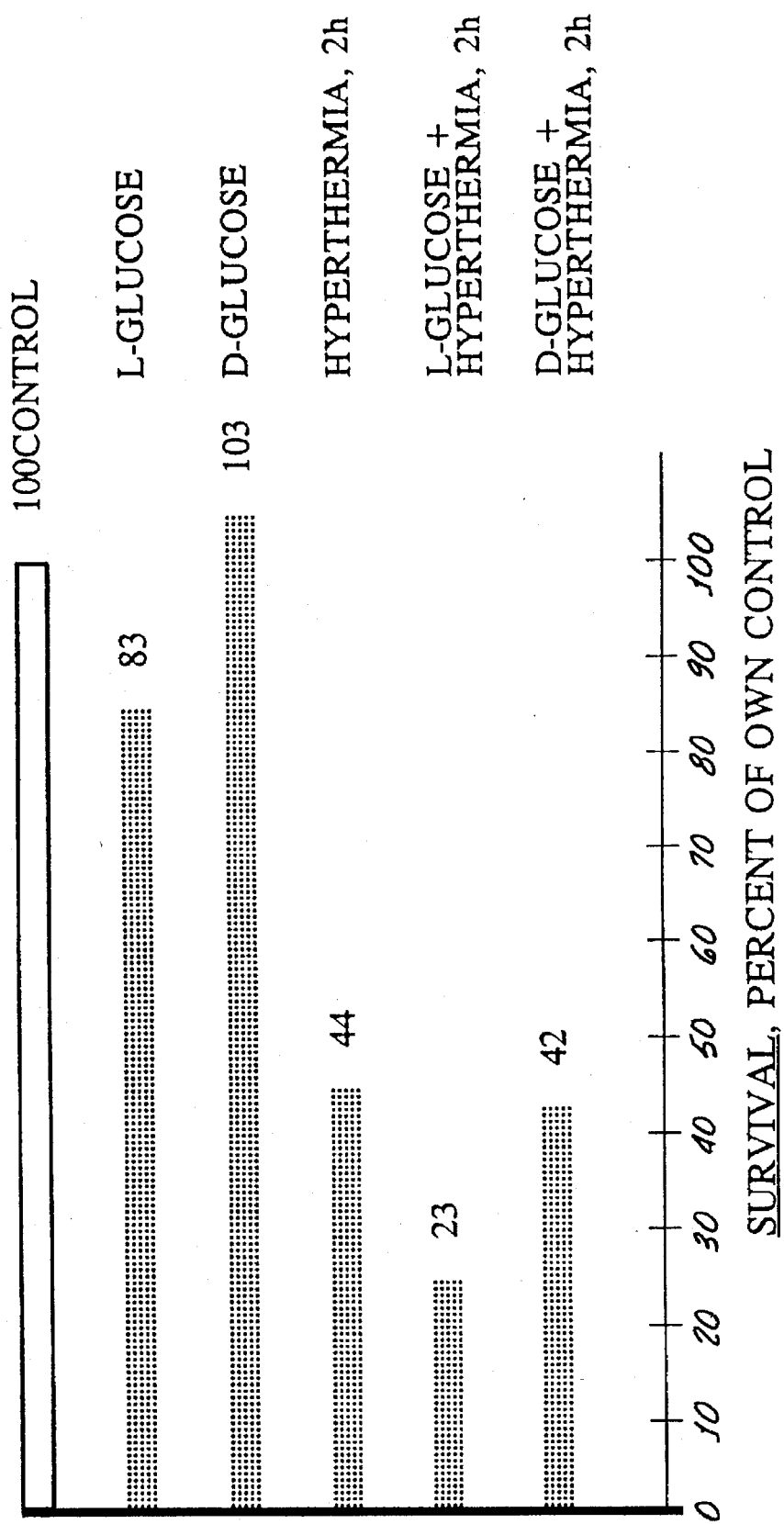
FIG. 10 represents the cytotoxic effects exhibited by both stereoisomers of glucose during hyperthermic treatments of CaOv cells. The heat therapy was conducted at 41° C. under hypoxic conditions for two hours.

These results are supported by the data for cell survival graphically represented in FIGS. 9 and 10. The survival of cells treated with heat in the presence of L-glucose was much lower than those treated with heat alone. Further, the survival rate of cells treated with heat in the presence of L-glucose was lower under hypoxic conditions than in the presence of oxygen. Again this corresponds to the reduction of growth rates exhibited in FIGS. 7 and 8. Under hypoxic conditions the survival rate for cells treated with heat in the presence of L-glucose was reduced to a quarter of the control survival. By way of comparison, the survival rate for cells treated with heat alone under hypoxic conditions was almost half. While the reduction in survival rate was not as pronounced under oxic conditions, the mortality of L-glucose treated cells was substantially higher than those treated with other methods.

In contrast, the survival of CaOv cells treated with D-glucose and hyperthermia demonstrates that the oxygenation of cells only exerts a slight effect on mortality. Heat treated cells cultured with D-glucose in both hypoxic and oxic conditions show survival rates of 98% and 95% in relation to hyperthermia alone. The results of these experiments clearly demonstrate that L-glucose enhances the cytotoxic and cytostatic effects of hyperthermic treatments on malignant cells.

EXAMPLE VI

L-Glucose Enhances the Cytostatic and Cytotoxic Effects of Radiation

Human Ovarian Cancer (CaOv)

Studies were completed to demonstrate the potentiation effect of L-glucose on neoplastic radiation therapy. The same human ovarian cancer cell line used in Example V was also used for this series of experiments. CaOv cells with and without 6 mg/ml L-glucose were subjected to various levels of gamma-irradiation.

CaOv cell cultures were started by inoculating 600 cells in 5 ml of 199 medium supplemented with 10% fetal calf serum and 40 µg/ml gentamicin. The flasks were incubated under oxic conditions with 5% $CO_2$ at 37° C. Two days later L-glucose was added to provide a concentration of 6 mg/ml. At the same time the selected flasks were irradiated at 8.4 rad/sec for a total of 2, 4 and 6 Gy respectively. Cell counts were conducted 48 hours after the radiation treatment and the growth rate was calculated as described above.

Figure 11:
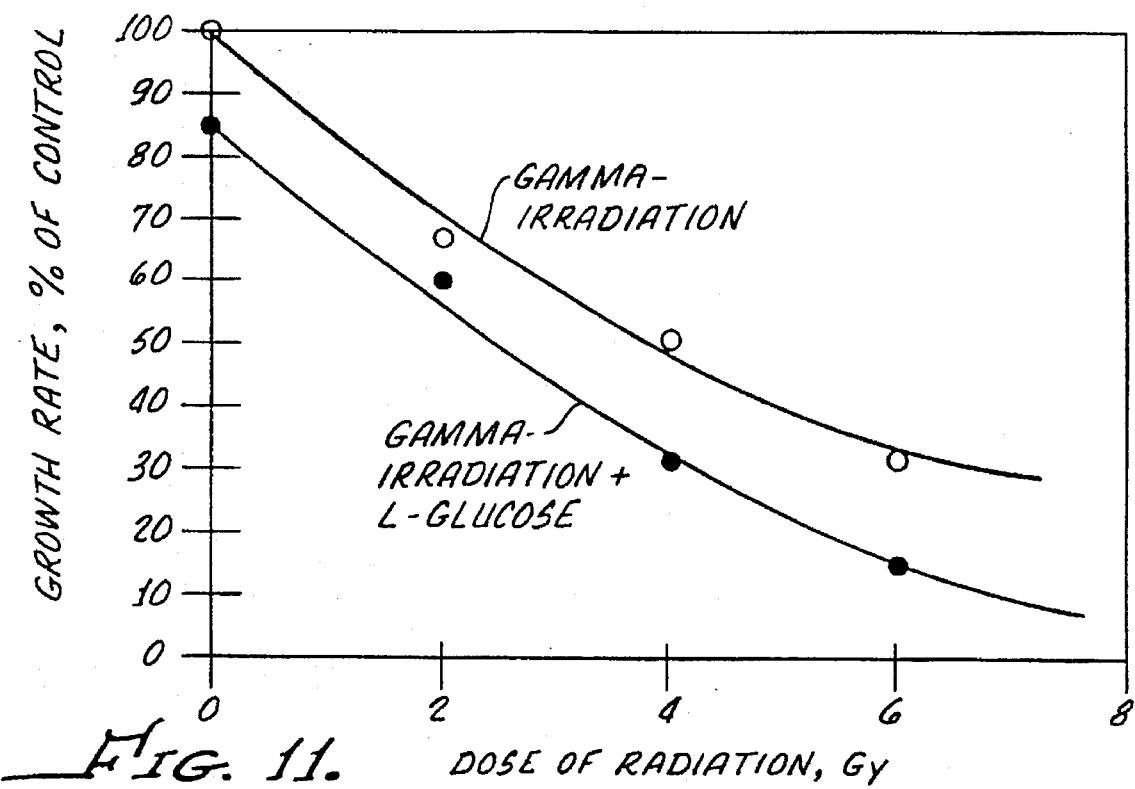
FIG. 11 shows the synergistic effects of 6 mg/ml L-glucose in combination with radiotherapy. Various doses of gamma-radiation were applied to CaOv cells with L-glucose present and CaOv cells without L-glucose present.

The results are presented in FIG. 11 and clearly demonstrate that L-glucose enhances the cytotoxic and cytostatic effects of radiotherapy on malignant cells. Potentiation such as this would allow the use of lower levels of radiation while obtaining the same results. This would greatly relieve the discomfort of those undergoing such therapy.

Having thus described representative embodiments of the present invention, it should be noted by those skilled in the art that the disclosures herein are exemplary only and that alternative, adaptations, and modifications may be made within the scope of the present invention. Accordingly, the present invention is not limited to the specific embodiments illustrated herein.

I claim:

1. A process for potentiating a radiotherapeutic treatment comprising:

administering L-glucose in conjunction with a radiotherapeutic treatment of a mammalian host afflicted with a population of neoplastic cells, said L-glucose being administered to said mammalian host in a dosage effective to potentiate said radiotherapeutic: treatment and to thereby reduce said population of neoplastic cells to a greater extent than said radiotherapeutic treatment alone.

2. The process of claim 1 wherein said L-glucose is administered with a pharmacologically acceptable carrier for said L-glucose.

3. The process of claim 2 wherein said carrier is aqueous.

4. The process of claim 1 wherein said radiotherapeutic treatment comprises irradiating said mammalian host to a total exposure of about 2 to 6 Gy.

5. A process for potentiating a hyperthermic treatment comprising:

administering L-glucose in conjunction with a hyperthermic treatment of a mammalian host afflicted with a population of neoplastic cells, said L-glucose being administered to said mammalian host in a dosage effective to potentiate said hyperthermic treatment and to thereby reduce said population of neoplastic cells to a greater extent than said hyperthermic treatment alone.

6. The process of claim 5 wherein said L-glucose is administered with a pharmacologically acceptable carrier for said L-glucose.

7. The process of claim 6 wherein said carrier is aqueous.

8. The process of claim 6 wherein said hyperthermic treatment is conducted at a temperature of about 41° C. to 43° C.

9. A process for potentiating a combined radiotherapeutic and hyperthermic treatment comprising:

administering L-glucose in conjunction with a combined radiotherapeutic and hyperthermic treatment of a mammalian host afflicted with a population of neoplastic cells, said L-glucose being administered to said mammalian host in a dosage effective to potentiate said combined radiotherapeutic and hyperthermic treatment.

10. The process of claim 9 wherein said L-glucose is administered with a pharmacologically acceptable carrier for said L-glucose.

11. The process of claim 10 wherein said carrier is aqueous.

12. The process of claim 9 wherein said radiotherapeutic treatment comprises irradiating said mammalian host to a total exposure of about 2 to 6 Gy.

13. The process of claim 9 wherein said hyperthermic treatment is conducted at a temperature of about 41° C. to 43° C.

* * * * *